United States Patent [19]
Walters

[11] Patent Number: 6,019,659
[45] Date of Patent: Feb. 1, 2000

[54] HEATED STUFFED TOY

[76] Inventor: Michael B. Walters, 700 NE. 26th Ter. #604, Miami, Fla. 33137

[21] Appl. No.: 09/109,196

[22] Filed: Jul. 2, 1998

[51] Int. Cl.$^7$ .................................. A63H 3/02; H05B 1/00
[52] U.S. Cl. ............................ 446/72; 446/369; 446/484; 219/200
[58] Field of Search .............................. 446/72, 73, 484, 446/369; 219/200, 201, 211, 212, 217, 528, 529

[56] References Cited

U.S. PATENT DOCUMENTS

| | | |
|---|---|---|
| 1,558,278 | 10/1925 | Phillips . |
| 1,896,663 | 2/1933 | Collins . |
| 4,404,460 | 9/1983 | Kerr ........................................ 219/211 |
| 5,906,763 | 5/1999 | Warren Van Deventer Wheeler ... 219/386 |

*Primary Examiner*—Robert A. Hafer
*Assistant Examiner*—Laura Fossum

[57] ABSTRACT

A heated stuffed toy for providing warmth to a user. The heated stuffed toy includes a body member having a stuffed interior and an outer layer configured to resemble a predetermined figure. A heating element for providing heat when energized is provided in the interior of the body. The heating element is positioned adjacent the outer layer of the body member in a serpentine arrangement extending over the entire body member including the extremities of the body member.

16 Claims, 2 Drawing Sheets

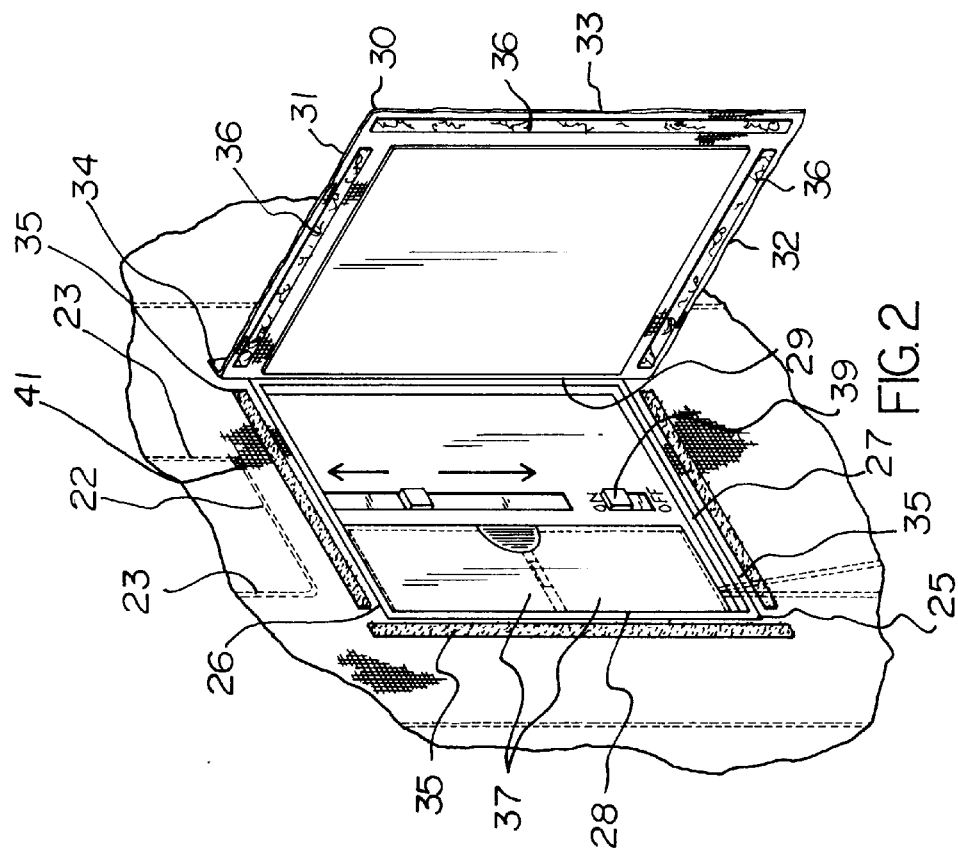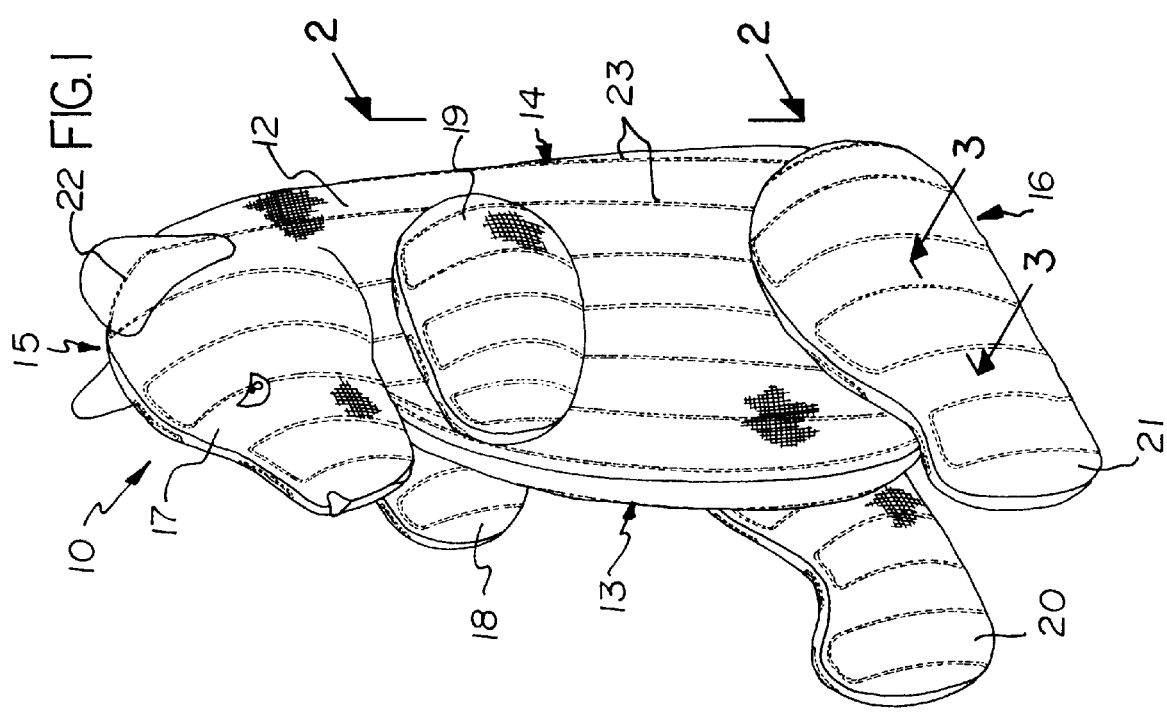

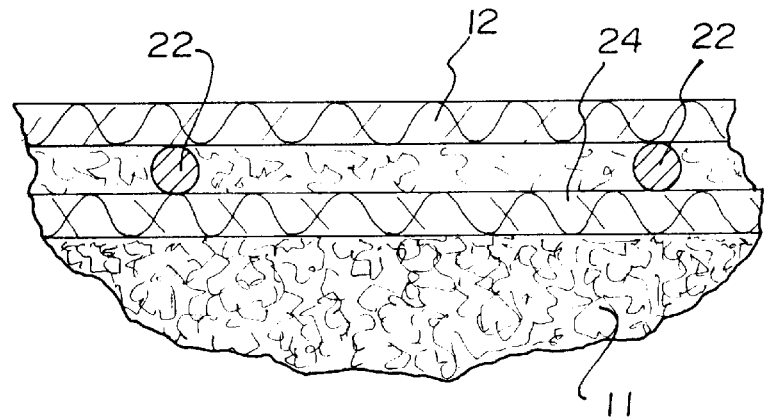
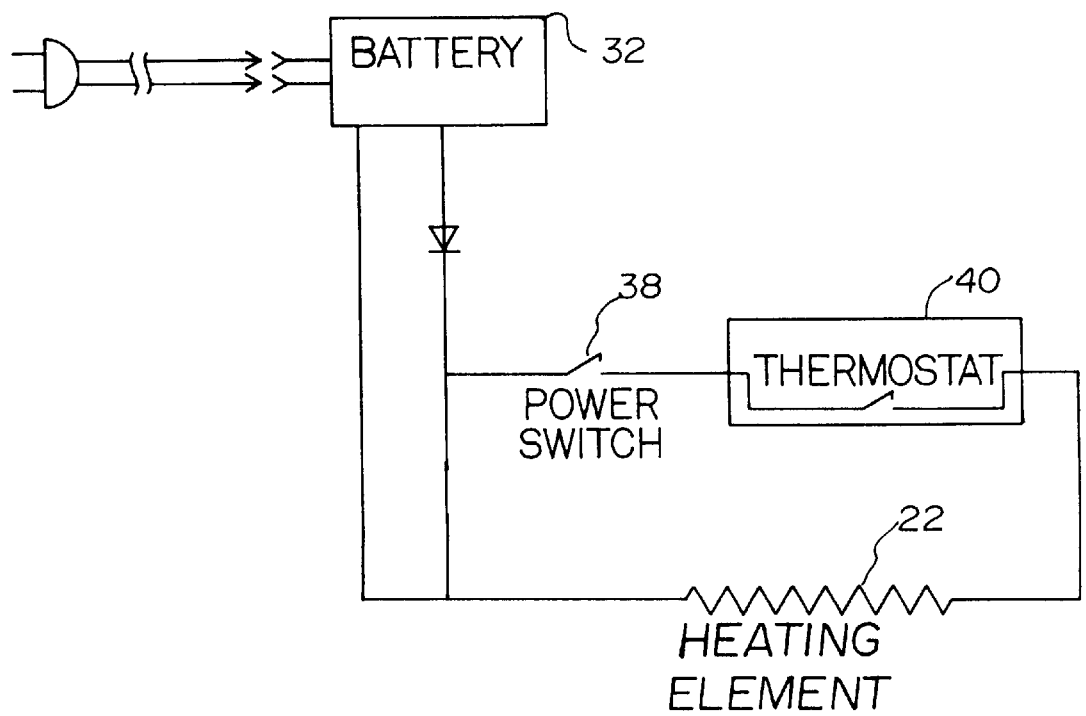

HEATED STUFFED TOY

BACKGROUND OF THE INVENTION

1. Field of the Invention

The present invention relates to heated stuffed toys and more particularly pertains to a new heated stuffed toy for providing warmth to a user.

2. Description of the Prior Art

The use of heated stuffed toys is known in the prior art. More specifically, heated stuffed toys heretofore devised and utilized are known to consist basically of familiar, expected and obvious structural configurations, notwithstanding the myriad of designs encompassed by the crowded prior art which have been developed for the fulfillment of countless objectives and requirements.

Known prior art heated stuffed toys include U.S. Pat. No. 4,954,676; U.S. Pat. No. 4,714,445; U.S. Pat. No. 4,694,829; U.S. Pat. No. 4,979,923; U.S. Pat. No. 3,184,886; and U.S. Pat. No. Des. 375,766.

While these devices fulfill their respective, particular objectives and requirements, the aforementioned patents do not disclose a new heated stuffed toy. The inventive device includes a body member having a stuffed interior and an outer layer configured to resemble a predetermined figure. A heating element for providing heat when energized is provided in the interior of the body. The heating element is positioned adjacent the outer layer of the body member in a serpentine arrangement extending over the entire body member including the extremities of the body member.

In these respects, the heated stuffed toy according to the present invention substantially departs from the conventional concepts and designs of the prior art, and in so doing provides an apparatus primarily developed for the purpose of providing warmth to a user.

SUMMARY OF THE INVENTION

In view of the foregoing disadvantages inherent in the known types of heated stuffed toys now present in the prior art, the present invention provides a new heated stuffed toy construction wherein the same can be utilized for providing warmth to a user.

The general purpose of the present invention, which will be described subsequently in greater detail, is to provide a new heated stuffed toy apparatus and method which has many of the advantages of the heated stuffed toys mentioned heretofore and many novel features that result in a new heated stuffed toy which is not anticipated, rendered obvious, suggested, or even implied by any of the prior art heated stuffed toys, either alone or in any combination thereof.

To attain this, the present invention generally comprises a body member having a stuffed interior and an outer layer configured to resemble a predetermined figure. A heating element for providing heat when energized is provided in the interior of the body. The heating element is positioned adjacent the outer layer of the body member in a serpentine arrangement extending over the entire body member including the extremities of the body member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention. Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new heated stuffed toy apparatus and method which has many of the advantages of the heated stuffed toys mentioned heretofore and many novel features that result in a new heated stuffed toy which is not anticipated, rendered obvious, suggested, or even implied by any of the prior art heated stuffed toys, either alone or in any combination thereof.

It is another object of the present invention to provide a new heated stuffed toy which may be easily and efficiently manufactured and marketed.

It is a further object of the present invention to provide a new heated stuffed toy which is of a durable and reliable construction.

An even further object of the present invention is to provide a new heated stuffed toy which is susceptible of a low cost of manufacture with regard to both materials and labor, and which accordingly is then susceptible of low prices of sale to the consuming public, thereby making such heated stuffed toy economically available to the buying public.

Still yet another object of the present invention is to provide a new heated stuffed toy which provides in the apparatuses and methods of the prior art some of the advantages thereof, while simultaneously overcoming some of the disadvantages normally associated therewith.

Still another object of the present invention is to provide a new heated stuffed toy for providing warmth to a user.

Yet another object of the present invention is to provide a new heated stuffed toy which includes a body member having a stuffed interior and an outer layer configured to resemble a predetermined figure. A heating element for providing heat when energized is provided in the interior of the body. The heating element is positioned adjacent the outer layer of the body member in a serpentine arrangement extending over the entire body member including the extremities of the body member.

Still yet another object of the present invention is to provide a new heated stuffed toy that has an adjustable temperature control for controlling the amount of heat given off by the toy.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic front perspective view of a new heated stuffed toy according to the present invention.

FIG. 2 is a schematic partial back perspective view of the present invention taken from the vantage of line 2—2 of FIG. 1.

FIG. 3 is a schematic cross sectional view of the present invention taken from line 3—3 of FIG. 1.

FIG. 4 is a schematic electrical diagram of the present invention.

DESCRIPTION OF THE PREFERRED EMBODIMENT

With reference now to the drawings, and in particular to FIGS. 1 through 4 thereof, a new heated stuffed toy embodying the principles and concepts of the present invention and generally designated by the reference numeral 10 will be described.

As best illustrated in FIGS. 1 through 4, the heated stuffed toy 10 generally comprises a body member 10 having a stuffed interior 11 and an outer layer 12 configured to resemble a predetermined figure. A heating element 22 for providing heat when energized is provided in the interior 11 of the body. The heating element 22 is positioned adjacent the outer layer 12 of the body member 10 in a serpentine arrangement extending over the entire body member 10 including the extremities 17,18,19,20,21 of the body member 10.

In closer detail, the body member 10 has a stuffed interior 11 and an outer layer 12 configured to resemble a predetermined figure. Preferably, the predetermined figure resembles an animal. Ideally, the predetermined figure resembles a teddy bear. The body member 10 has a front 13, a back 14, a top 15, a bottom 16, and a plurality of extremities 17,18,19,20,21. The extremities include a head portion 17, and a number of limb portions 18,19,20,21. The head portion is located at the top 15 of the body member 10. The head and limb portions 17,18,19,20,21 are configured to resemble the head and limbs of the animal of the predetermined figure.

A heating element 22 for providing heat when energized is provided in the interior 11 of the body member 10. The heating element 22 is positioned adjacent the outer layer 12 of the body member 10 in a serpentine arrangement extending over the entire body member 10 including the extremities 17,18,19,20,21 of the body member 10. The serpentine arrangement has a plurality of elongate coils with each of the coils having an elongate portion 23 extending generally parallel to the other elongate portions 23 of the other coils of the serpentine arrangement. The elongate portions 23 of the coils are preferably generally equally spaced apart from the elongate portions 23 of adjacent coils. Preferably, each of the elongate portions 23 of the coils has a length extending in a vertical direction between the top 15 and bottom 16 of the body member 10.

Optionally, the body member 10 may include an insulating secondary layer 24 provided between the outer layer 12 and the interior 11 of the body member 10. The heating element 22 is sandwiched between the outer layer 12 and the insulating secondary layer 24 such that the coils of the heating element 22 are in contact with the outer layer 12 and the insulating secondary layer 24. The insulating secondary layer 24 preferably comprises a heat reflecting material such that heat from the heating element 22 is reflected away from the secondary heating layer.

The body member 10 has a cavity in the interior 11 of the body member 10. The cavity is positioned adjacent the back 14 of the body member 10 with the back 14 of the body member 10 having an opening 25 into the cavity. The opening 25 into the cavity has a generally rectangular periphery including a pair of ends 26,27, and a pair of sides 28,29 extending between the ends of the periphery. In an ideal embodiment, the cavity has a depth from the outer layer 12 into the interior 11 of the body member 10 of about 2 inches, and the opening 25 has a length defined between the ends 26,27 of the periphery of the opening 25 of about 5 inches and a width defined between the sides 28,29 of the periphery of the opening 25 of about 3 inches.

A cover flap 30 substantially covers the opening 25 into the cavity. The cover flap 30 is generally rectangular and has a pair of end edges 31,32 and a pair of side edges 33,34. One of the side edges 34 of the cover flap 30 is pivotally coupled to the outer layer 12 of the body member 10 adjacent one of the sides 29 of the periphery of the opening 25 into the cavity. A fastener preferably detachably attaches the end edges 32,33 and the other of the side edges 33 of the cover flap 30 to the outer layer 12 of the body member 10. Preferably, the fastener comprises a hook and loop fastener has a pair of complementary portions with one of the portions of the hook and loop fastener provided on the cover flap 30 and the other of the complementary portions provided on the outer layer 12 of the body member 10. Ideally, the hook and loop fastener comprises a number of complementary strips 35,36. The strips of one of the complementary portions 35 are provided on the outer layer 12 adjacent the ends 26,27 and the other side 28 of the periphery of the opening 25 into the cavity while the strips of the other of the complementary portion 36 are provided on the end edges 31,32 and a corresponding side edge 33 of the cover flap 30.

A power source is electrically connected to the heating element 22 to provided energy to the heating element 22. The power source preferably comprises a battery provided in the cavity. Ideally, the power source comprises a pair of rechargeable batteries 37 which are removable from the cavity through the opening 25 into the cavity. A switch 38 is electrically connected to the heating element 22 for permitting selective energization of the heating element 22. The switch 38 has an actuator 39 provided in the cavity for permitting a user to selectively energize the heating element 22. A thermostat 40 is electrically connected to the heating element 22 to selective control the amount of heat provided by the heating element 22. The thermostat 40 has an temperature actuator 41 provided in the cavity for permitting a user to selectively control the amount of heat provided by the heating element 22.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A heated stuffed toy, comprising:
   a body member having a stuffed interior and an outer layer configured to resemble a predetermined animate figure;
   said body member having a front, a back, a top, a bottom, and a plurality of extremities;
   a heating element for providing heat when energized being provided in said interior of said body, said heating element being positioned adjacent said outer layer of said body member in a serpentine arrangement extending substantially throughout all of said body member including said extremities of said body member.

2. The heated stuffed toy of claim 1, wherein said predetermined figure resembles an animal.

3. The heated stuffed toy of claim 1, wherein said predetermined figure resembles a teddy bear.

4. The heated stuffed toy of claim 1, wherein said serpentine arrangement has a plurality of elongate coils, each of said coils having an elongate portion extending generally parallel to elongate portions of the other coils of said serpentine arrangement, said elongate portions of said coils being generally equally spaced apart from the elongate portions of adjacent coils.

5. The heated stuffed toy of claim 4, wherein each of said elongate portions of said coils has a length extending in a direction between said top and bottom of said body member.

6. The heated stuffed toy of claim 1, wherein said body member has an insulating secondary layer provided between said outer layer and said interior of said body member, said heating element being positioned between said outer layer and said insulating secondary layer such that said coils of said heating element are in contact with said outer layer and said insulating secondary layer.

7. The heated stuffed top of claim 1, wherein said body member has a cavity in said interior of said body member, said cavity being positioned adjacent said back of said body member, said back of said body member having an opening into said cavity.

8. The heated stuffed toy of claim 7, wherein said opening into said cavity has a generally rectangular periphery including a pair of ends, and a pair of sides extending between said ends of said periphery, and wherein a cover flap substantially covers said opening into said cavity, said cover flap being generally rectangular and having a pair of end edges and a pair of side edges, one of said side edges of said cover flap being pivotally coupled to said outer layer of said body member adjacent one of said sides of said periphery of said opening into said cavity.

9. The heated stuffed toy of claim 8, wherein a fastener detachably attaches said end edges and the other of said side edges of said cover flap to said outer layer of said body member.

10. The heated stuffed toy of claim 9, wherein said fastener comprises a hook and loop fastener having a pair of complementary portions, one of said portions of said hook and loop fastener being provided on said cover flap, the other of said complementary portions being provided on said outer layer of said body member.

11. The heated stuffed toy of claim 10, wherein each of said portions of said hook and loop fastener includes a number of complementary strips, said strips of one of said complementary portions being provided on said outer layer adjacent said ends and said other side of said periphery of said opening into said cavity, said strips of the other of said complementary portion being provided on said end edges and a corresponding side edge of said cover flap.

12. The heated stuffed toy of claim 8, wherein said cavity has a depth from said outer layer into said interior of said body member of about 2 inches, wherein said opening has a length defined between said ends of said periphery of said opening of about 5 inches, and wherein said opening has a width defined between said sides of said periphery of said opening of about 3 inches.

13. The heated stuffed toy of claim 7, wherein a power source is electrically connected to said heating element to provide energy to said heating element, said power source comprising a battery provided in said cavity.

14. The heated stuffed toy of claim 13, wherein said power source comprises a pair of rechargeable batteries, said rechargeable batteries being removable from said cavity through said opening into said cavity.

15. The heated stuffed toy of claim 7, wherein a switch is electrically connected to said heating element for permitting selective energization of said heating element, said switch having an actuator provided in said cavity for permitting a user to selectively energize said heating element, and wherein a thermostat is electrically connected to said heating element to selective control the amount of heat provided by said heating element, said thermostat having an temperature actuator being provided in said cavity for permitting a user to selectively control the amount of heat provided by said heating element.

16. A heated stuffed toy, comprising:
   a body member having a stuffed interior and an outer layer configured to resemble a predetermined figure, wherein said predetermined figure resembles a teddy bear;
   said teddy bear having a front, a back, a top, a bottom, and a plurality of extremities, said extremities including a head portion, and a number of limb portions, said head portion being located at said top of said body member, said head and limb portions being configured to resemble the head and limbs of said teddy bear;
   a heating element for providing heat when energized being provided in said interior of said body, said heating element being positioned adjacent said outer layer of said body member in a serpentine arrangement extending over said body member including said extremities of said body member;
   said serpentine arrangement having a plurality of elongate coils, each of said coils having an elongate portion extending generally parallel to elongate portions of the other coils of said serpentine arrangement, said elongate portions of said coils being generally equally spaced apart from the elongate portions of adjacent coils, each of said elongate portions of said coils having a length extending in a direction between said top and bottom of said body member;

said body member having an insulating secondary layer provided between said outer layer and said interior of said body member, said heating element being positioned between said outer layer and said insulating secondary layer such that said coils of said heating element are in contact with said outer layer and said insulating secondary layer, said insulating secondary layer comprising a heat reflecting material such that heat from said heating element is reflected away from said secondary heating layer;

said body member having a cavity in said interior of said body member, said cavity being positioned adjacent said back of said body member, said back of said body member having an opening into said cavity;

said opening into said cavity having a generally rectangular periphery including a pair of ends, and a pair of sides extending between said ends of said periphery;

said cavity having a depth from said outer layer into said interior of said body member of about 2 inches;

wherein said opening has a length defined between said ends of said periphery of said opening of about 5 inches, wherein said opening has a width defined between said sides of said periphery of said opening of about 3 inches;

a cover flap substantially covering said opening into said cavity, said cover flap being generally rectangular and having a pair of end edges and a pair of side edges;

one of said side edges of said cover flap being pivotally coupled to said outer layer of said body member adjacent one of said sides of said periphery of said opening into said cavity;

a fastener detachably attaching said end edges and the other of said side edges of said cover flap to said outer layer of said body member, wherein said fastener comprises a hook and loop fastener; having a pair of complementary portions, one of said portions of said hook and loop fastener being provided on said cover flap, the other of said complementary portions being provided on said outer layer of said body member;

wherein each of said portions of said hook and loop fastener includes a number of complementary strips, said strips of one of said complementary portions being provided on said outer layer adjacent said ends and said other side of said periphery of said opening into said cavity, said strips of the other of said complementary portion being provided on said end edges and a corresponding side edge of said cover flap;

a power source being electrically connected to said heating element to provide energy to said heating element, said power source comprising a battery provided in said cavity, wherein said power source comprises a pair of rechargeable batteries, said rechargeable batteries being removable from said cavity through said opening into said cavity;

a switch being electrically connected to said heating element for permitting selective energization of said heating element, said switch having an actuator provided in said cavity for permitting a user to selectively energize said heating element; and a thermostat being electrically connected to said heating element to selective control the amount of heat provided by said heating element, said thermostat having an temperature actuator being provided in said cavity for permitting a user to selectively control the amount of heat provided by said heating element.

* * * * *